United States Patent [19]

Gante et al.

[11] Patent Number: 4,632,933
[45] Date of Patent: Dec. 30, 1986

[54] SULFUR-CONTAINING IMIDAZOLE DERIVATIVES

[75] Inventors: Joachim Gante, Darmstadt-Arheilgen; Helmut Prücher, Heppenheim; Helmut Wahlig, Darmstadt; Volkmar Rudolph, Seeheim, all of Fed. Rep. of Germany

[73] Assignee: Merck Patent Gesellschaft mit beschränkter Haftung, Darmstadt, Fed. Rep. of Germany

[21] Appl. No.: 583,552

[22] Filed: Feb. 24, 1984

[30] Foreign Application Priority Data

Feb. 25, 1983 [DE] Fed. Rep. of Germany ....... 3306646

[51] Int. Cl.⁴ .................. C07D 233/60; A61K 31/415
[52] U.S. Cl. ..................................... 514/399; 548/341
[58] Field of Search ......................... 548/341; 514/399

[56] References Cited

U.S. PATENT DOCUMENTS 4,036,970 7/1977 Walker et al. ..................... 424/273
4,078,071 3/1978 Walker ............................... 514/399

Primary Examiner—Joseph Paul Brust
Attorney, Agent, or Firm—Millen & White

[57] ABSTRACT

New sulfur-containing imidazole derivatives of the general formula

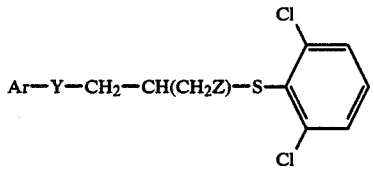

in which Ar is a phenyl radical which is unsubstituted or substituted by one or two halogen atoms, Y is O or S, and Z is a 1-imidazolyl or 2-methyl-1-imidazolyl radical, and their physiologically acceptable acid addition salts, have antimycotic and antibacterial activity.

7 Claims, No Drawings

SULFUR-CONTAINING IMIDAZOLE DERIVATIVES

BACKGROUND OF THE INVENTION

This invention relates to new sulfur-containing imidazole derivatives having valuable pharmacological properties.

Certain compounds are disclosed in U.S. Pat. No. 4,036,970 having a general formula

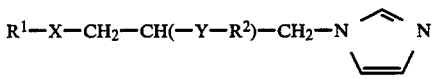

in which $R^1$ can be phenyl or phenyl substituted by one or two halogen atoms, X can also be O or S, Y can also be S, and $R^2$ can also be a phenyl group substituted by one or two halogen atoms. Examples with $R^2$=3,4-dichlorophenyl and $R^2$=2,4-dichlorophenyl are indicated in this patent.

SUMMARY OF THE INVENTION

It is an object of this invention to provide new compounds having valuable pharmacological properties. Upon further study of the specification and appended claims, further objects and advantages of this invention will become apparent to those skilled in the art.

These objects have been attained by providing new sulfur-containing imidazole derivatives of formula I

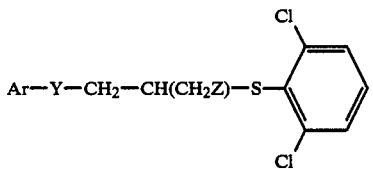

in which Ar is a phenyl radical which is unsubstituted or substituted by one or two halogen atoms, Y is O or S, and Z is a 1-imidazolyl or a 2-methyl-1-imidazolyl radical, and their acid addition salts.

DETAILED DISCUSSION

In U.S. Pat. No. 4,036,970, there is no indication whatever of the possibility that $R^2$ may also be a 2,6-dichlorophenyl group and, in particular, that -Y-$R^2$ may also be a 2,6-dichlorophenylthio group. Thus, there is no possibility of the expert obtaining any pointer to the compounds of the present formula I from this patent specification; these compounds are not evident from the U.S. Patent Specification.

It has been found that the compounds of the formula I have valuable pharmacological properties and are well tolerated. In particular, antimycotic and antibacterial effects (in vitro and in vivo) occur, for example against thread fungi, such as *Microsporum audouini*, *Microsporum gypseum*, *Epidermophyton floccosum*, *Trichophyton rubrum*, *Trichophyton tonsurans*, *Trichophyton mentagrophytes*, *Blastomyces brasiliensis* and *Histoplasma capsulatum*; mould fungi, such as *Aspergillus fumigatus*, *Aspergillus niger* and *Scopulariopsis fusca*; yeasts, such as *Candida albicans*, *Candida parapsilosis* and *Cryptococcus neoformans*; actinomycetes, such as *Nocardia minutissima* and *Nocardia asteroides*; Gram-negative and Gram-positive bacteria, such as *Staphylococcus aureus*, *Streptococcus pyogenes*, *Streptococcus faecalis*, *Corynebacterium acnes*, *Erysiphelothrix insidiosa*, *Proteus vulgaris*, *Proteus mirabilis*, *Salmonella cholerae-suis*, *Pasteurella multocida*, *Pseudomonas aeruginosa*, *Mycobacterium ranae* and *Escherichia coli*. The compounds also act against systemic fungal infections; in addition, effects against protozoa, in particular against trichomonads, for example against *Trichomonas vaginalis*, occur.

These efficacies can be determined in vitro by, for example, the customary agar dilution methods, but they can also be determined in vivo, for example on mice, rats or rabbits.

In addition, antiinflammatory effects are shown, and these can be demonstrated in, for example, the adjuvant arthritis test by the method of Newbould (Brit. J. Pharmacol. 21 (1963) pages 127–136) on rats. Furthermore, there are shown antiarteriosclerotic effects and effects lowering the level of cholesterol (demonstrable in the serum of rats by the method of Levine et al., Automation in Analytical Chemistry, Technicon Symposium 1967, Mediad, N.Y., pages 25–28) and lowering the level of triglycerides (demonstrable by the method of Noble and Campbell, Clin. Chem. 16 (1970) pages 166–170). In addition, analgesic, antipyretic, enzyme-inducing, fibrinolytic and platelet-aggregation-inhibiting effects can be detected by methods customary for this purpose.

The compounds of the formula I and their physiologically acceptable acid addition salts can thus be used as active compounds in medicaments and as intermediates for the preparation of other active compounds for medicaments.

The invention relates to imidazole derivatives of the formula I and their salts.

In the radicals indicated above, Ar is preferably p-chlorophenyl, but is also phenyl, o-chlorophenyl, 2,4- or 2,6-dichlorophenyl, also m-chlorophenyl, 2,3-, 2,5-, 3,4- or 3,5-dichlorophenyl, o-, m- or p-fluorophenyl, 2,3-, 2,4-, 2,5-, 2,6-, 3,4- or 3,5-difluorophenyl, o-, m- or p-bromophenyl, 2,3-, 2,4-, 2,5-, 2,6-, 3,4- or 3,5-dibromophenyl, o-, m- or p-iodophenyl, 2,4-, 2,5-, 2,6-or 3,5-diiodophenyl, 2-fluoro-4-chlorophenyl, 2-chloro-4-fluorophenyl, 2-chloro-6-fluorophenyl or 2-chloro-4-bromophenyl. The radical Y is preferably O. The radical Z is preferably 1-imidazolyl.

Accordingly, the invention particularly relates to those compounds of the formula I in which at least one of the radicals Ar, Y and/or Z has one of the preferred meanings indicated in the foregoing.

The invention also relates to a process for the preparation of the compounds of the formula I and their acid addition salts, characterized in that a compound of the general formula II

in which X is Cl, Br, I, OH or derivatized OH, and Ar, Y and Z have the indicated meanings, is reacted with 2,6-dichlorothiophenol or one of its salts, or in that a compound of the general formula III

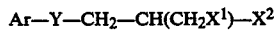

in which one of the radicals $X^1$ and $X^2$ is X, and the other of these radicals is

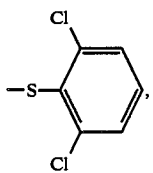

and Ar, X and Y have the indicated meanings, is reacted with an imidazole of the general formula H—Z (IV) or one of its metal derivatives, or in that a compound of the general formula V

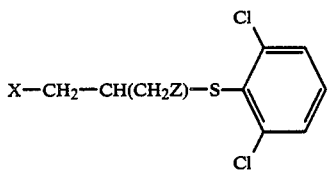

in which X and Z have the indicated meanings, is reacted with a compound of the general formula VI Ar—Y—H        VI in which Ar and Y have the indicated meanings, or one of its salts, and/or in that, where desired, a base of the general formula I is converted into one of its acid addition salts by treatment with an acid.

The preparation of the compounds of the formula I otherwise takes place by methods known per se, as are described in the literature (for example in the standard works, such as Houben-Weyl, Methoden der organischen Chemie (Methods of Organic Chemistry) published by Georg-Thieme, Stuttgart), that is to say under the reaction conditions known and suitable for the reactions mentioned. For this, it is also possible to make use of variants which are known per se but are not mentioned here in detail.

In all general formulae in the foregoing and subsequent text, Ar, Y and Z have the meaning indicated for formula I unless expressly indicated otherwise.

Some of the starting materials for the preparation of the compounds of the formula I are known. All can be prepared by processes known per se. Where desired, the starting materials can also be formed in situ in such a manner that they are not isolated from the reaction mixture but are immediately reacted further to give the compounds of the formula I.

The compounds of the formula I are preferably obtained by reacting a compound of the formula II with 2,6-dichlorothiophenol or one of its salts, for example the Na or K salt, which can also be formed in situ from the thiophenol and a base, for example sodium or potassium hydroxide.

In the compounds of the formula II, X is preferably Cl, Br or I. If X is a derivatized OH group, then it is preferably an alkylsulfonyloxy or arylsulfonyloxy group having, in particular, up to 10 C atoms, for example methanesulfonyloxy, benzenesulfonyloxy or p-toluenesulfonyloxy.

As a rule, the starting materials of the formula II are new. All can be prepared by, for example, reaction of epichlorohydrin with phenolates or thiophenolates of the formula Ar-Y-Na to give 1,2-epoxy-3-ArY-propanes, reaction with imidazoles of the formula H—Z or their metal derivatives to give hydroxy compounds of the formula Ar—Y—CH$_2$—CHOH—CH$_2$—Z and, where desired, conversion into the 2-chloro or 2-bromo compound (with SOCl$_2$ or PBr$_3$) or into an appropriate sulfonic ester (for example into the methanesulfonate with methanesulfonyl chloride).

The imidazole derivatives of the formula II are preferably reacted with 2,6-dichlorothiophenol or its salts at temperatures between about 0° and 100° in the presence of an inert solvent, for example an alcohol, such as methanol, ethanol, isopropanol or n-butanol, an ether, such as diethyl ether, diisopropyl ether, tetrahydrofuran or dioxane, a hydrocarbon, such as benzene, toluene or xylene, an amide, such as dimethylformamide, a sulfoxide, such as dimethyl sulfoxide, or a ketone, such as acetone.

The imidazole derivatives of the formula I can also be obtained by reacting a thioether of the formula III with an imidazole of the formula H—Z (IV) or one of its metal derivatives, for example the Na or K derivative.

The starting materials of the formula III can be prepared by, for example, reacting the abovementioned 1,2-epoxy-3-ArY-propanes with 2,6-dichlorothiophenol and, where desired, converting the OH group into the appropriate derivative, for example the chloride, bromide or methanesulfonate.

They comprise thioethers of the formulae IIIa and IIIb:

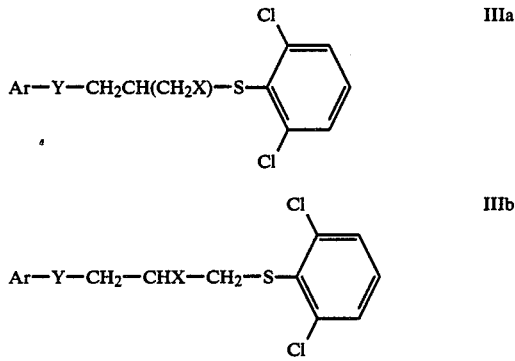

The same final product I is produced from both. The course of the reaction presumably goes via the intermediate sulfonium salt VII

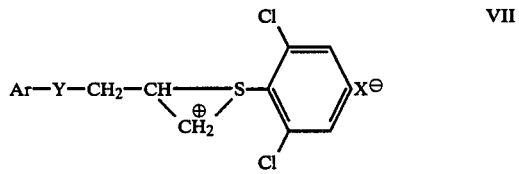

The starting materials of the formula IV (imidazole and 2-methylimidazole) are known.

The reaction of the thioethers of the formula III with the imidazoles of the formula IV is preferably carried out at temperatures between about 0° and about 250°, preferably between about 20° and 120°. It is possible to work without a solvent or in the presence of one of the inert solvents mentioned. Where desired, a catalyst can be present, for example sodium amide, which can also be produced in situ from sodium and liquid ammonia, also bases such as sodium carbonate, potassium carbonate, sodium bicarbonate or potassium bicarbonate. An excess of the compound of the formula IV is preferably used; this excess can also serve as the solvent (in the melt).

The compounds of the formula I can also be obtained by reacting the imidazole derivatives of the formula V with the phenols or thiophenols of the formula VI.

The compounds of the formula V can be obtained by, for example, reacting 3-bromopropionic acid with an imidazole of the formula H—Z (IV) to give a 3-Z-propionic acid, brominating to give a 2-bromo-3-Z-propionic acid, reacting with Na 2,6-dichlorothiophenolate to give a 2-(2,6-dichlorophenylthio)-3-Z-propionic acid, reducing with $LiAlH_4$ to give an alcohol of the formula V (X=OH) and, where desired, further reacting with $SOCl_2$, $PBr_3$ or a sulfonyl chloride. As a rule, the compounds of the formula VI are known.

The phenol or thiophenol of the formula VI is preferably initially converted into a salt, in particular, a metal salt, for example an alkali metal salt (Li, Na or K salt). It is possible to react the phenol or thiophenol with a reagent forming a metal salt, for example an alkali metal (for example Na), an alkali metal hydride or amide (for example LiH or NaH; $NaNH_2$ or $KNH_2$), an alkali metal alcoholate (in which the alcohol moiety preferably has 1-4 C atoms, for example lithium, sodium or potassium methylate, ethylate or tert.-butylate), an organometallic compound (for example butyllithium, phenyllithium or phenylsodium), or a metal hydroxide, carbonate or bicarbonate (for example of Li, Na, K or Ca). The preparation of the phenolate or thiophenolate is advantageously carried out in the presence of one of the solvents mentioned or a mixture of these solvents.

The reaction of the phenolate or thiophenolate with the compound V is preferably carried out in the presence of a diluent, for example that solvent which has been used for the preparation of the phenolate or thiophenolate, but it is possible for it to be replaced by another solvent or diluted with one. The reaction is preferably carried out at temperatures between 20° and 120°.

It is also possible to form the phenolate or thiophenolate in situ. In this case, the phenol or thiophenol VI and the compound V are allowed to react together in the presence of a base. A particularly preferred method comprises heating the compounds V and VI together with an alcoholic sodium hydroxide solution for about 5 to 15 hours.

A base of the formula I which has been obtained can be converted with an acid into the relevant acid addition salt in a customary manner. Suitable for this reaction are preferably strong acids which provide physiologically acceptable salts. Thus, it is possible to use inorganic acids, for example sulfuric acid, hydrogen halide acids, such as hydrochloric acid or hydrobromic acid, phosphoric acids, such as orthophosphoric acid, nitric acid and sulfamic acid, but also organic acids, specifically aliphatic, alicyclic, araliphatic, aromatic or heterocyclic monobasic or polybasic carboxylic, sulfonic or sulfuric acids, such as formic acid, malonic acid, succinic acid, pimelic acid, fumaric acid, maleic acid, lactic acid, tartaric acid, malic acid, salicylic acid, 2- or 3-phenylpropionic acid, citric acid, gluconic acid, ascorbic acid, methanesulfonic and ethanesulfonic acid, ethanedisulfonic acid, 2-hydroxyethanesulfonic acid, benzenesulfonic acid, p-toluenesulfonic acid, naphthalenemonosulfonic and naphthalenedisulfonic acids and lauryl sulfuric acid. Salts with acids which are not physiologically acceptable (for example the picrates) are suitable for the isolation and purification of the bases of the formula I.

Where desired, the free bases of the formula I can be liberated from their salts by treatment with strong bases, such as sodium or potassium hydroxide or sodium or potassium carbonate.

The compounds of the formula I contain one center of asymmetry. They usually exist in the form of a racemate. Racemates which have been obtained can be resolved into their optical antipodes by mechanical or chemical methods known per se. Preferably, diastereomers are formed from the racemic mixture by reaction with an optically active resolving agent. Examples of suitable resolving agents are optically active acids, such as the D and L forms of tartaric acid, diacetyltartaric acid, dibenzoyltartaric acid, mandelic acid, malic acid, lactic acid or the various optically active camphorsulfonic acids, such as $\beta$-camphorsulfonic acid, but also camphanic acid.

Of course, it is also possible to obtain optically active compounds of the formula I by the methods described above when the starting materials used are already optically active.

The invention also relates to the use of the new compounds of the formula I and their physiologically acceptable acid addition salts for the production of pharmaceutical formulations, particularly by non-chemical routes. For this purpose, they can be converted into a suitable dosage form together with at least one solid, liquid and/or semi-liquid vehicle or auxiliary and optionally together with one or more further active compound(s).

The invention also relates to agents, in particular pharmaceutical formulations, containing a compound of the formula I and/or one of its physiologically acceptable acid addition salts.

These formulations can be used as medicaments in human and veterinary medicine. Suitable vehicles are organic or inorganic substances which are suitable, in particular, for enteral (for example oral), parenteral or topical administration and which do not react with the new compounds, for example water, vegetable oils, hydrocarbons, such as alkylated naphthalenes, halogenated hydrocarbons, such as $CF_2Cl_2$ (for example for aerosols), benzyl alcohols, polyethylene glycols, glycerol triacetate, gelatins, carbohydrates, such as lactose or starch, magnesium stearate, talc and vaseline. In particular, uncoated and coated tablets, capsules, syrups, juices or drops are used for oral administration, suppositories for rectal administration, vaginal suppositories for intravaginal and solutions, preferably oily or aqueous solutions, but also suspensions, emulsions or implants, for parenteral administration, and solutions, lotions, emulsions, sprays (aerosols), ointments, creams, pastes or powders for topical administration. The new compounds can also be freeze-dried and the lyophilizates obtained used to prepare, for example, products for injection. The indicated formulations can be sterilized and/or contain auxiliaries, such as lubricants, preservatives, stabilizers and/or wetting agents, emulsifiers, salts to modify the osmotic pressure, buffer substances, colorants, flavorings and/or aromatic substances. Where desired, they can also contain one or more other active compounds, for example one or more antibiotics, vitamins and/or other antimycotics.

As a rule, the new compounds are administered in analogy to known antimycotics available commercially (for example clotrimazole or miconazole), preferably in doses between about 2 and 600 mg, in particular between 5 and 200 mg, per dosage unit. The daily dose is preferably between about 0.1 and 20 mg/kg of body weight. In this context, the low doses preferably apply to parenteral administration and the higher to oral administration. Oral or parenteral administration is preferred, in particular for systemic candida infections, for example infections with Candida albicans, but also for South American blastomycosis and all organic mycoses, especially those caused by candida species, Actinomycetes, mold fungi, other fungi and infections by bacteria, in particular Gram-positive bacteria. A high activity over a wide range of dilution can be detected on topical administration combined with vehicles suitable for this. For example, concentrations of the active compound between about 0.1 and 10 per cent by weight, based on the weight of the product used, are shown to be effective for controlling fungi or bacteria. Concentrations of about 1 to 3 per cent by weight are preferred.

Oral administration of the new compounds is preferred when they are used as antiinflammatory or lipid-lowering agents. As a rule, they are then administered in analogy to known antiinflammatory (for example indometacin) or lipid-lowering (for example bezafibrat) agents preferably in doses between about 5 and 500 mg, in particular between 20 and 200 mg, per dosage unit. The daily dose is preferably between about 0.2 and 20 mg/kg of body weight.

However, the specific dose in all cases for each patient depends on a wide variety of factors, for example on the efficacy of the specific compound employed, on the age, body weight, general state of health, sex, diet, time and route of administration, on the rate of excretion, the medicament combination and the severity of the particular disease. Thus, in individual cases, it is also possible to use higher or lower concentrations or doses than those indicated.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

In the examples which follow, "customary work-up" denotes: where necessary, water or dilute sodium hydroxide solution is added, the mixture is extracted with an organic solvent which is immiscible with water (for example benzene, chloroform or dichloromethane), the organic phase is separated off, dried over sodium sulfate, filtered, evaporated and the product is purified by chromatography and/or crystallization. Ihe product can also be purified by crystallization of one of its acid addition salts.

EXAMPLE 1

A mixture of 27.1 g of 1-p-chlorophenoxy-2-chloro-3-(1-imidazolyl)propane (obtainable by reaction of epichlorohydrin with Na p-chlorophenolate to give 1-p-chlorophenoxy-2,3-epoxypropane, reaction with imidazole to give 1-p-chlorophenoxy-3-(1-imidazolyl)-2-propanol and reaction with $SOCl_2$), 17.9 g of 2,6-dichlorothiophenol and 7 g of $K_2CO_3$ in 1 liter of acetone is boiled, with stirring, for 4 hours, then evaporated, worked up as usual and 1-p-chlorophenoxy-2-(2,6-dichlorophenylthio)-3-(1-imidazolyl)propane is obtained. Hydrochloride (Ia), m.p. 75°–177°.

The following may be obtained analogously:
1-phenoxy-2-(2,6-dichlorophenylthio)-3-(1-imidazolyl)-propane, hydrochloride, m.p. 168°–170°
1-o-fluorophenoxy-2-(2,6-dichlorophenylthio)-3-(1-imidazolyl)propane
1-m-fluorophenoxy-2-(2,6-dichlorophenylthio)-3-(1-imidazolyl)propane
1-p-fluorophenoxy-2-(2,6-dichlorophenylthio)-3-(1-imidazolyl)propane, hydrochloride, m.p. 153°–155°
1-o-chlorophenoxy-2-(2,6-dichlorophenylthio)-3-(1-imidazolyl)propane, hydrochloride, m.p. 179°–181°
1-m-chlorophenoxy-2-(2,6-dichlorophenylthio)-3-(1-imidazolyl)propane
1-o-bromophenoxy-2-(2,6-dichlorophenylthio)-3-(1-imidazolyl)propane
1-m-bromophenoxy-2-(2,6-dichlorophenylthio)-3-(1-imidazolyl)propane
1-p-bromophenoxy-2-(2,6-dichlorophenylthio)-3-(1-imidazolyl)propane
1-p-iodophenoxy-2-(2,6-dichlorophenylthio)-3-(1-imidazolyl)propane
1-(2,4-difluorophenoxy)-2-(2,6-dichlorophenylthio)-3-(1-imidazolyl)propane
1-(2,3-dichlorophenoxy)-2-(2,6-dichlorophenylthio)-3-(1-imidazolyl)propane
1-(2,4-dichlorophenoxy)-2-(2,6-dichlorophenylthio)-3-(1-imidazolyl)propane, nitrate, m.p. 135°–136°
1-(2,5-dichlorophenoxy)-2-(2,6-dichlorophenylthio)-3-(1-imidazolyl)propane
1-(2,6-dichlorophenoxy)-2-(2,6-dichlorophenylthio)-3-(1-imidazolyl)propane
1-(3,4-dichlorophenoxy)-2-(2,6-dichlorophenylthio)-3-(1-imidazolyl)propane
1-(3,5-dichlorophenoxy)-2-(2,6-dichlorophenylthio)-3-(1-imidazolyl)propane
1-(2,4-dibromophenoxy)-2-(2,6-dichlorophenylthio)-3-(1-imidazolyl)propane
1-phenylthio-2-(2,6-dichlorophenylthio)-3-(1-imidazolyl)-propane
1-o-chlorophenylthio-2-(2,6-dichlorophenylthio)-3-(1-imidazolyl)propane
1-p-chlorophenylthio-2-(2,6-dichlorophenylthio)-3-(1-imidazolyl)propane, hydrochloride, m.p. 150°–152°
1,2-bis-(2,6-dichlorophenylthio)-3-(1-imidazolyl)propane
1-phenoxy-2-(2,6-dichlorophenylthio)-3-(2-methyl-1-imidazolyl)propane
1-o-fluorophenoxy-2-(2,6-dichlorophenylthio)-3-(2-methyl-1imidazolyl)propane
1-m-fluorophenoxy-2-(2,6-dichlorophenylthio)-3-(2-methyl-1imidazolyl)propane
1-p-fluorophenoxy-2-(2,6-dichlorophenylthio)-3-(2-methyl-1imidazolyl)propane
1-o-chlorophenoxy-2-(2,6-dichlorophenylthio)-3-(2-methyl-1imidazolyl)propane
1-m-chlorophenoxy-2-(2,6-dichlorophenylthio)-3-(2-methyl-1imidazolyl)propane
1-p-chlorophenoxy-2-(2,6-dichlorophenylthio)-3-(2-methyl-1-imidazolyl)propane, hydrochloride, m.p. 162°–163°
1-o-bromophenoxy-2-(2,6-dichlorophenylthio)-3-(2-methyl-1-imidazolyl)propane
1-m-bromophenoxy-2-(2,6-dichlorophenylthio)-3-(2-methyl-1-imidazolyl)propane
1-p-bromophenoxy-2-(2,6-dichlorophenylthio)-3-(2-methyl-1-imidazolyl)propane 1-p-iodophenoxy-2-(2,6-dichlorophenylthio)-3-(2-methyl-1-imidazolyl)propane
1-(2,4-difluorophenoxy)-2-(2,6-dichlorophenylthio)-3-(2-methyl-imidazolyl)propane
1-(2,3-dichlorophenoxy)-2-(2,6-dichlorophenylthio)-3-(1-imidazolyl)propane
1-(2,4-dichlorophenoxy)-2-(2,6-dichlorophenylthio)-3-(2-methyl-1-imidazolyl)propane
1-(2,5-dichlorophenoxy)-2-(2,6-dichlorophenylthio)-3-(2-methyl-1-imidazolyl)propane
1-(2,6-dichlorophenoxy)-2-(2,6-dichlorophenylthio)-3-(2-methyl-1-imidazolyl)propane
1-(3,4-dichlorophenoxy)-2-(2,6-dichlorophenylthio)-3-(2-methyl-1-imidazolyl)propane
1-(3,5-dichlorophenoxy)-2-(2,6-dichlorophenylthio)-3-(2-methyl-1-imidazolyl)propane
1-(2,4-dibromophenoxy)-2-(2,6-dichlorophenylthio)-3-(2-methyl-1-imidazolyl)propane
1-phenylthio-2-(2,6-dichlorophenylthio)-3-(1-imidazolyl)propane
1-o-chlorophenylthio-2-(2,6-dichlorophenylthio)-3-(2-methyl-1-imidazolyl)propane
1-p-chlorophenylthio-2-(2,6-dichlorophenylthio)-3-(2-methyl-1-imidazolyl)propane and
1,2-bis(2,6-dichlorophenylthio)-3-(2-methyl-1-imidazolyl)propane.

EXAMPLE 2

A mixture of 44.2 g of 1-p-chlorophenoxy-2-methylsulfonyloxy-3-(2,6-dichlorophenylthio)propane [obtainable by reaction of 1-p-chlorophenoxy-2,3-epoxypropane with Na 2,6-dichlorothiophenolate to give 1-p-chlorophenoxy-3-(2,6-dichlorophenylthio)-2-propanol and reaction with methanesulfonyl chloride], 20.4 g of imidazole and 250 ml of dimethylformamide is heated to 100° for 2 hours and then worked up as usual. Ia of m.p. 175°–177° is obtained.

The other imidazole derivatives mentioned in Example 1 may be obtained analogously.

EXAMPLE 3

38.2 g of 1-chloro-2-(2,6-dichlorophenylthio)-3-p-chlorophenoxypropane [obtainable by reaction of 3-bromo-propionic acid with Na p-chlorophenolate to give 3-p-chlorophenoxypropionic acid, bromination to give 2-bromo-3-p-chlorophenoxypropionic acid, reaction with Na 2,6-dichlorothiophenolate to give 2-(2,6-dichlorophenylthio)-3-p-chlorophenoxypropionic acid, LiAlH$_4$ reduction to give the alcohol and reaction with SOCL$_2$]is heated at 120° with 40 g of imidazole for 5 hours, then cooled, worked up as usual and Ia of m.p. 175°–177° is obtained.

The other imidazole derivatives mentioned in Example 1 may be obtained analogously.

EXAMPLE 4

A mixture of 12.9 g of p-chlorophenol, 36.6 g of 1-bromo-2-(2,6-dichlorophenylthio)-3-(1-imidazolyl)propane [obtainable by reaction of 3-bromopropionic acid with imidazole to give 3-(1-imidazolyl)propionic acid, bromination to give 2-bromo-3-(1-imidazolyl)propionic acid, reaction with Na 2,6-dichlorothiophenolate to give 2-(2,6-dichlorophenylthio)-3-(1-imidazolyl)propionic acid, reduction with LiAlH$_4$ to give the corresponding alcohol, and reaction with PBr$_3$], 8 g of NaOH and 400 ml of ethanol is heated at 100° for 10 hours. The mixture is evaporated, worked up as usual and Ia of m.p. 175°–177° is obtained.

The other imidazole derivatives mentioned in Example 1 may be obtained analogously.

The examples which follow relate to pharmaceutical formulations which contain imidazole derivatives of the formula I or their acid addition salts:

EXAMPLE A

Tablets

A mixture of 1 kg of Ia, 4 kg of lactose, 1.2 kg of potato starch, 0.2 kg of talc and 0.1 kg of magnesium stearate is compressed in a customary manner to produce tablets such that each tablet contains 100 mg of active compound.

EXAMPLE B

Coated tablets

Tablets are compressed in analogy to Example A, and they are then coated in a customary manner with a coating comprising sucrose, potato starch, talc, tragacanth and colorant.

EXAMPLE C

Capsules 10 kg of Ia are filled in a customary manner into hard gelatine capsules so that each capsule contains 50 mg of active compound.

EXAMPLE D

Ampoules

A solution of 1 kg of Ia in 30 liters of double-distilled water is sterilized by filtration, filled into ampoules, freeze-dried under sterile conditions and sealed sterile. Each ampoule contains 10 mg of active compound.

EXAMPLE E

Ointment 2 kg of Ia is dissolved in a warm liquefied mixture of 40 kg of polyethylene glycol 400 and 58 kg of polyethylene glycol 1500. The solution is stirred while cooling and is used as an ointment for the treatment of fungal and bacterial infections.

EXAMPLE F

Cream

A mixture of 20 kg of Ia, 200 kg of polyethylene glycol 1000 monocetyl ether, 50 kg of polyethylene glycol 1500 monocetyl ether, 150 kg of vaseline, 50 kg of liquid paraffin and 2 kg of sorbic acid is heated in a customary manner, allowed to cool and 528 kg of water is stirred in.

EXAMPLE G

Cream

A mixture of 2 kg of Ia, 5 kg of 1,2-propanediol, 5 kg of glycerol stearate, 5 kg of spermaceti, 10 kg of isopropyl myristate and 4 kg of polysorbate 60 is warmed, allowed to cool and 69 kg of water is stirred in.

EXAMPLE H

Solution 2 kg of Ia is dissolved in 98 kg of 1,2-propanediol. The solution is used for the treatment of fungal and bacterial infections.

EXAMPLE I

Spray

The spray comprises a solution of 1 (part by weight) of Ia, 10 of isopropyl myristate, 15 of liquid paraffin, 30 of ethanol and 44 of isopropanol.

Tablets, coated tablets, capsules, ampoules, ointments, creams, solutions and sprays which contain one or more of the other active compounds of the formula I and/or their physiologically acceptable salts may be obtained analogously.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A sulfur-containing imidazole derivative of the formula

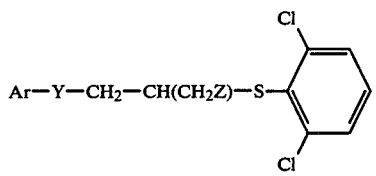

wherein Ar is phenyl substituted by one chloro atom; Y is O; and Z is 1-imidazolyl; or a physiologically acceptable acid addition salt thereof.

2. A compound of claim 1 wherein Ar is p-chlorophenyl.

3. 1-p-Chlorophenoxy-2-(2,6-dichlorophenylthio)-3-(1-imidazolyl)propane, a compound of claim 1.

4. An antimycotic composition comprising an amount of a compound of claim 1 effective as an antimycotic and a pharmaceutically acceptable carrier.

5. A composition of claim 4 wherein the amount of said compound is 2–600 mg.

6. A method of achieving an antimycotic effect in a patient comprising administering an antimycotic effective amount of a compound of claim 1 to the patient.

7. A method of achieving an antibacterial effect in a patient comprising administering an antibacterial effective amount of a compound of claim 1 to the patient.

* * * * *